United States Patent
Melzig et al.

(10) Patent No.: US 7,459,555 B2
(45) Date of Patent: *Dec. 2, 2008

(54) PHOTOCHROMIC NAPHTHOPYRANS

(75) Inventors: Manfred Melzig, Wessling (DE); Claudia Mann, Munich (DE); Udo Weigand, Munich (DE)

(73) Assignee: Rodenstock GmbH, Munich (DE)

(*) Notice: Subject to any disclaimer, the term of this patent is extended or adjusted under 35 U.S.C. 154(b) by 1357 days.

This patent is subject to a terminal disclaimer.

(21) Appl. No.: 10/013,518

(22) Filed: Dec. 13, 2001

(65) Prior Publication Data

US 2002/0052499 A1 May 2, 2002

Related U.S. Application Data

(62) Division of application No. 09/485,921, filed as application No. PCT/EP99/04239 on Jun. 18, 1999, now Pat. No. 6,342,459.

(30) Foreign Application Priority Data

Jun. 19, 1998 (DE) .............. 198 27 411

(51) Int. Cl.
- C07D 265/30 (2006.01)
- C07D 405/00 (2006.01)
- C07D 311/78 (2006.01)
- C07D 307/77 (2006.01)

(52) U.S. Cl. .......... 544/171; 546/282.1; 549/384; 549/298

(58) Field of Classification Search .......... 549/384, 549/298; 544/171; 546/282.1
See application file for complete search history.

(56) References Cited

U.S. PATENT DOCUMENTS

| | | | |
|---|---|---|---|
| 3,567,605 | A | 3/1971 | Becker |
| 3,973,966 | A * | 8/1976 | Flannery et al. .......... 96/4 |
| 5,066,818 | A | 11/1991 | Gemert |
| 5,458,814 | A | 10/1995 | Kumar |
| 5,573,712 | A | 11/1996 | Kumar |
| 5,645,767 | A | 7/1997 | Van Gemert |
| 5,650,098 | A | 7/1997 | Kumar |
| 5,651,923 | A | 7/1997 | Kumar |
| 5,656,206 | A | 8/1997 | Knowles |
| 5,658,500 | A | 8/1997 | Kumar |
| 5,658,501 | A | 8/1997 | Kumar |
| 5,698,141 | A | 12/1997 | Kumar |
| 5,723,072 | A | 3/1998 | Kumar |
| 6,342,459 | B1 * | 1/2002 | Melzig et al. .......... 501/13 |

FOREIGN PATENT DOCUMENTS

| | | |
|---|---|---|
| DE | 19902771.4 | 12/1991 |
| WO | WO 98/04937 | 2/1998 |
| WO | WO 99/15518 | 4/1999 |
| WO | WO 99/20619 | 4/1999 |

OTHER PUBLICATIONS

Auwers, K.v. et al., "Zur Zerreissbarkeit der Kohlenstoffkette in Bernsteinsaeure-Derivaten" *Chem. Ber.* (1935) 68:349-352.

Bachmann, W.E. et al., "The Synthesis of 6-Hydroxy-17-equilenone (an Isomer of Equilenin) and Two of its Homologs" *J. Chem. Soc.* (1940) 62:2750-2757.

Kon, G.A.R. et al., "Syntheses of Polycyclic Compounds related to the Sterols. Part V. Methoxy- and Hydroxy-derivatives of Phenanthrene" *J. Chem. Soc.* (1936) pp. 187-191.

Kotsuki, H. et al., "High Pressure Organic Chemistry; XI.[1] A New Convenient Synthesis of Aromatic Amines from Activated Phenols" *Synthesis* (1990) pp. 1145-1147.

Sasaki, T. et al., "Molecular Design by Cycloaddition Reactions. VI.[1] Observation of the Enone-n-methane Moiety in Photochemical [1,3] and [3,3] Sigmatropic Rearrangements" *J. Org. Chem.* (1973) 38:4100-4106.

* cited by examiner

*Primary Examiner*—Janet L Andres
*Assistant Examiner*—Binta M Robinson
(74) *Attorney, Agent, or Firm*—Crowell & Moring LLP

(57) ABSTRACT

The present invention relates to photochromic 2H-naphtho[1,2-b]pyrans as well as their use in synthetic resins of all types, especially for ophthalmic purposes. In particular, the present invention relates to photochromic naphthopyran compounds, for which a further ring system is bonded to the f side of the naphthopyran. The inventive photochromic dyes generally have the general formula (I)

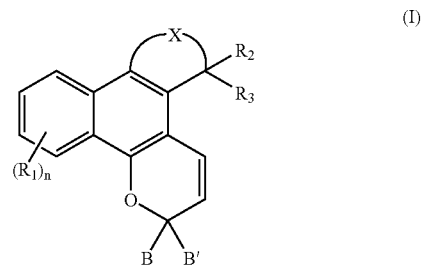

wherein n, $R_1$, $R_2$, $R_3$, X, B and B' are defined as in claim 1. The inventive compounds are distinguished by good darkening and decolorizing properties and a very good service life.

8 Claims, No Drawings

PHOTOCHROMIC NAPHTHOPYRANS

The present invention relates to photochromic 2H-naphtho[1,2-b]pyrans as well as to their use in synthetic resins of all types, particularly for ophthalmic purposes. In particular, the present invention relates to photochromic naphthopyran compounds, for which a further ring system is bonded to the f side of the naphthopyran.

Different classes of dyes are known which, when irradiated with light of particular wavelengths, particularly sunlight, change their color reversibly. This is due to the fact that, because energy is supplied in the form of light, these dye molecules change over into a stimulated colored state, which they leave once again when the supply of energy is interrupted in order to return to their colorless or at least hardly colored normal state. These photochromic dyes include, for example, the naphthopyrans, which have already been described with different substituents in the state of the art.

Pyrans, especially naphthopyrans and larger ring systems derived from these, are photochromic compounds, which until now have been the object of intensive investigations. Although the first patent was filed already in 1966 (U.S. Pat. No. 3,567,605), compounds, which are suitable for use in eyeglass lenses, were developed only in the 1990s.

A suitable class of pyran compounds is, for example, the 2,2-diaryl-2H-naphtho[1,2-b]pyrans. 2H-Naphtho[1,2-b]pyrans generally are orange to red photochromic compounds, which are decolorized very slowly after they have become darker, such as the Comparison Examples 4 and 5 and the Comparison Example A in U.S. Pat. No. 5,066,818.

Attempts were made to achieve improvements here by substituting the carbon atoms in the 5 and 6 positions of the naphthalene part in the naphthopyran. Compounds of this type are described, for instance, in U.S. Pat. Nos. 5,458,814, 5,573,712, 5,650,098, 5,656,206, 5,658,500 and 5,658,501 and in WO 98/04937. Since there was a need for further improvement, 2H-naphtho[1,2-b]pyran systems were described for the first time in U.S. Pat. No. 5,651,923. At the f side of the naphthopyran, that is, at the naphthalene part, these compounds have condensed benzothieno, benzofurano or indolo system, the benzothieno, benzofurano and indolo systems being bound to the naphthalene via the heterocyclic portion. It is disadvantage of the three naphthofuro[2',3':3,4]- and naphthofuro[3',2':3,4]-naphtho[1,2-b]pyrans of Examples 4, 5 and 6 in U.S. Pat. No. 5,651,923, that these decolorize very slowly and/or have a very slight photochromic efficiency ($\Delta$OD). Indolonaphthopyrans also decolorize similarly slowly. In the WO 99/20619, pentahydrophenanthro[9,10-b]pyrans and tetrahydrocyclopenta[c]naphtho[1,2-b]pyrans are described, which also have the disadvantage that their decolorizing rate is slow and therefore unsatisfactory for practical use in sunglasses.

In addition, an expensive and long synthesis route is required for the systems described. Furthermore, due to the possibility of conjugating with a further aromatic ring (system), a bathochromic shift relative to the basic absorption of the naphthopyran system may be observed, which frequently is undesirable. This applies likewise for the compounds in U.S. Pat. No. 5,645,767, which relate exclusively to indeno[2,1-f]naphtho[1,2-b]pyrans. Further continuations may be found in U.S. Pat. Nos. 5,698,141 and 5,723,072, which additionally have condensed unsubstituted, monosubstituted or disubstituted heterocyclic systems.

The known compounds are however associated with disadvantages, which affect the wearing comfort of the eyeglasses when these photochromic dyes are used in sunglass lenses. The known dyes have an inadequate long-wave absorption in the excited as well as in the not-excited state. This leads to problems even when these compounds are combined with other photochromic dyes. The temperature sensitivity with respect to the darkening is too high. At the same time, the decolorization frequently is too slow. In addition, the dyes described have an inadequate service life and, with that, in insufficient durability in sunglass lenses. The latter becomes noticeable in a rapidly abating efficiency and/or in severe yellowing. Moreover, the synthesis of the compounds, described in the state of the art, usually is expensive and lengthy and generally does not permit further optically interesting properties, such as a nonlinearity, to be incorporated into the respective structures.

Accordingly, it is an object of the present invention to make available new photochromic compounds, which have improved properties in comparison to the structures described in the state of the art. The photochromic compounds are to be distinguished particularly owing to the fact that they have faster kinetics in the light-stimulated state, than do comparable compounds from the state of the art, and exhibit a better behavior in the service life test.

This objective is accomplished by the objects, characterized in the claims. In particular, photochromic 2H-naphtho[1,2-b]pyrans of the general formula (I) are made available

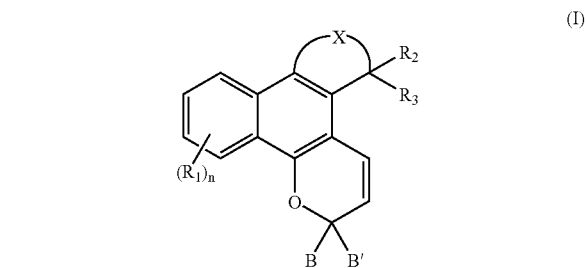

(I)

wherein

X represents a ring element with 2 to 4 saturated and/or unsaturated carbon atoms, of which not more than one can be replaced by a hetero atom, selected from the group comprising O, S and $NR_4$, $R_4$ being a linear or branched $C_1$ to $C_6$ alkyl group, a substituted or unsubstituted $C_5$ to $C_7$ cycloalkyl group, a substituted or unsubstituted phenyl group or a substituted or unsubstituted benzyl group;

$R_1$ is a substituent, selected from group A, comprising a $C_1$ to $C_6$ alkyl group, a $C_1$ to $C_6$ alkoxy group, a $C_3$ to $C_7$ cycloalkyl group, which may have one or more hetero atoms, a phenyl group, a hydroxy group, bromine, chlorine and fluorine, n being 0, 1 or 2;

$R_2$, $R_3$ independently of one another are groups, selected from group G, comprising hydrogen, hydroxy, a $C_1$ to $C_6$ alkyl group, a $C_1$ to $C_6$ alkoxy group, a $C_3$ to $C_7$ cycloalkyl group, an unsubstituted, monosubstituted and disubstituted phenyl group and an unsubstituted, monosubstituted and disubstituted naphthyl group and the aromatic groups, selected from group C, comprising benzene, naphthalene, phenanthrene, pyridine, quinoline, furan, thiophene, pyrrol, benzofuran, benzothiophene, indol and carbazol, the substituent or substituents of the aforementioned aromatic groups being selected from group A;

or $R_2$ and $R_3$ together, with inclusion of the spiro carbon atom, form a 5-membered to 11-membered ring, to which one or several aromatic or heteroaromatic ring systems may be annellated, the aromatic or heteroaromatic ring system or systems being one of the aforementioned group C;

or $R_2$ and $R_3$ together represent an oxygen atom with formation of a carbonyl group;

with the proviso that, when X is —$(CH_2)_2$— or —$(CH_2)_3$— and $R_2$ and $R_3$ are not at the same time hydrogen;

B, B' are selected independently of one another from the following groups a), b) or c), wherein a) are mono-, di- and trisubstituted aryl groups, the aryl group being phenyl or naphthyl;

b) are unsubstituted, mono- and disubstituted heteroaryl groups, the heteroaryl group being pyridyl, furanyl, benzofuran-3-yl, benzofuran-3-yl, thienyl, benzothien-2-yl or benzothien-3-yl; the substituents of the aryl groups or the heteroaryl groups in a) and b) being selected from a group comprising hydroxy, amino, mono-($C_1$ to $C_6$)-alkylamino, di-($C_1$ to $C_6$)-alkylamino, mono- and diphenylamino, unsubstituted, monosubstituted or disubstituted at the aromatic ring, piperidinyl, morpholinyl, carbazolyl, unsubstituted, monosubstituted and disubstituted pyrryl, $C_1$ to $C_6$ alkyl, $C_1$ to $C_6$ alkoxy, bromine, chlorine and fluorine, wherein the aforementioned aromatic and heteroaromatic ring systems can be substituted with $C_1$ to $C_6$ alkyl, $C_1$ to $C_6$ alkoxy, bromine, chlorine and fluorine;

c) are structure units with the following formulas (V) and (W)

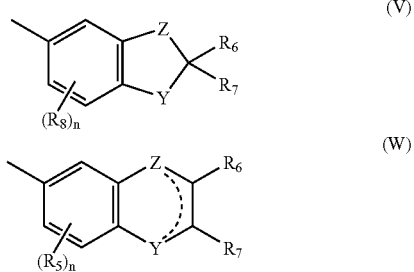

wherein

Y and Z, independently of one another are O, S, CH, $CH_2$ or $NR_8$, the $R_8$ group is selected from the group D comprising $C_1$ to $C_6$ alkyl, $C_1$ to $C_6$ acyl and hydrogen, and $R_5$ in each case is a substituent from group A, n being defined as above; and $R_6$ and $R_7$, independently of one another, are hydrogen and/or a $C_1$ to $C_6$ alkyl group, with the proviso that, when Y in formula (V) is $NR_8$, Z is a carbon atom;

or d) B and B' form with one another an unsubstituted, monosubstituted or disubstituted fluorene-9-ylidene group or a saturated hydrocarbon group, which is $C_3$ to $C_{12}$, spiro-monocyclic, $C_7$ to $C_{12}$ spiro-bicyclic and/or $C_7$-$C_{12}$ spiro-tricyclic, the fluoreno substituents being selected from Group A.

Pursuant to the invention, compounds, the absorption wavelengths of which are hardly shifted from those of the framework, but which, at the same time, show in a surprising manner a significantly improved decolorization in comparison to compounds of the state of the art, are prepared by a simple ring formation at the f side of the naphthopyran framework. Compared to the pentahydrophenanthro[9,10-b]pyrans and tetrahydrocyclopenta[c]-naphtho[1,2-b]pyrans, which are described in the WO 99/20619 and differ from the inventive napthyrans owing to the fact that an unsubstituted cyclopentane ring or an unsubstituted cyclohexane ring, in which X is —$(CH_2)_2$— or —$(CH_2)_3$— and $R_2$ and $R_3$ each are hydrogen, is linked at the f side of the naphthopyran framework, the inventive compounds exhibit a distinctly more rapid decolorization and significant improvements in the service life. Furthermore, yellowing no longer occurs in the case of the inventive compounds.

In a preferred embodiment, the carbon atoms in the X ring element are saturated, as a result of which corresponding cycloaliphatic ring systems, substituted with the $R_2$ and $R_3$ groups, are formed at the f side of the naphthopyran.

The carbon atoms in the X ring element may be unsubstituted, as well as monosubstituted or disubstituted. In the latter case, the substituents or substituents may be selected from group A consisting of $C_1$ to $C_6$ alkyl, $C_1$ to $C_6$ alkoxy, phenyl, bromine, chlorine and fluorine.

Pursuant to the present invention, photochromic 2H-naphtho[1,2-b]pyrans of formula (I) are also prepared, which structurally have spiro systems annellated at the f side of the naphthopyran system, the spiro system being formed by the ring system, formed by the ring element X at the f side of the naphthopyran, and the $R_2$ and $R_3$ group bound to the central spiro carbon atom. The $R_2$ and $R_3$ groups together with inclusion of the spiro carbon atoms, form a 5- to 11-membered ring and preferably a 5- to 7-membered ring, to which once again aromatic or heteroaromatic ring systems can be annellated. In other words, adjacent carbon atoms in the part of the spiro system, formed by $R_2$ and $R_3$, can belong to further ring systems, namely a ring system from the C group, consisting of benzene, naphthalene, phenanthrene, pyridine, quinoline, furan, thiophene, pyrrol, benzofuran, benzothiophene, indol and carbazol. Of course, these ring systems of group C can be unsubstituted as well as monosubstituted or disubstituted, the substituents being selected from the group A defined above.

Photochromic 2H-naphtho[1,2-b]pyrans, produced pursuant to the invention, have the following general formula (II),

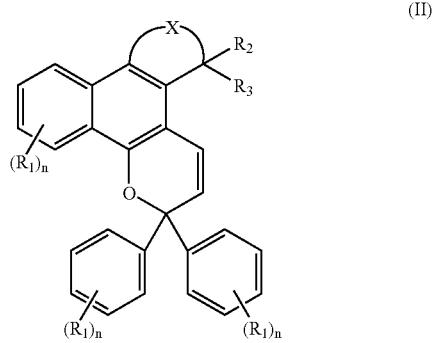

wherein n, $R_1$, $R_2$, $R_3$ and X are defined as above with the proviso that the $R_1$ groups and n in each case can be the same or different.

In a further embodiment, photochromic 2H-naphtho[1,2-b]pyrans are prepared, which have the following formula (III),

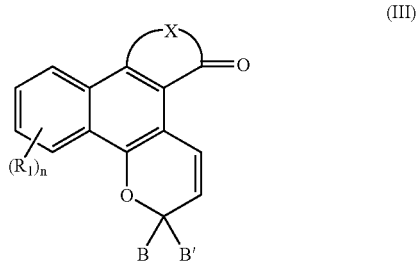

wherein n, $R_1$, X, B and B' are defined as above.

Especially preferred inventive compounds are:
1) spiro-9'-xanthene-5-[2-(4-methoxyphenyl)-2-phenyl-5,6,7,8-tetrahydro-6,6,7,7-tetramethyl-phenanthro[9,10-b]pyran]
2) spiro-9'-fluorene-5-{2-[4-(N-morpholinyl)phenyl]-2-phenyl-5,6,7,8-tetrahydrophenanthro[9,10-b]pyran}
3) 5-hydroxy-2,2,5-triphenyl-5,6,7,8-tetrahydro-phenanthro[9,10-b]pyran
4) spiro-9'-{(9,10-dihydroanthracene)-5-[2,2-bis(4-methoxyphenyl)]-cyclopenta[f]naphtho [1,2-b]pyran}
5) 2-[4-(N-morpholinyl)phenyl]-2-phenyl-5-oxo-cyclopenta[f]naphthopyran
6) 2-[4-(N-morpholinyl)phenyl]-2-phenyl-5,6,7,8-tetrahydro-5-oxo-phenanthro[9,10-b]pyran]
7) spiro-9'-fluorene-5-[2-(4-methoxyphenyl)-2-phenyl-cyclopenta-[f]naphtho[1,2-b]pyran]
8) spiro-9'-xanthene-5-{-2-[4-(N-morpholinyl)phenyl]-2-phenyl-5,6,7,8-tetrahydro-6,6,7,7,-tetramethyl-phenanthro[9,10-b]pyran}
9) spiro-9'-fluorene-5-[2-(4-methoxyphenyl)-2-phenyl-cyclohepta[f]naphtho[1,2-b]pyran] and
10) spiro-9'-fluorene-5-[2-(4-methoxyphenyl)-2-phenyl-oxepano[3,2-f]naphtho[1,2-b]pyran].

The inventive, photochromic 2H-naphtho[1,2-b]pyrans with the general formula (I) can be synthesized employing principles, which are basically known in the field. In this connection, reference is made particularly to the synthesis methods described in WO 99/15518 and in the German patent application 199 02 771.4. For example, the inventive photochromic 2H-naphtho[1,2-b]pyrans can be synthesized according to the following general outline of the reactions, without being limited to these, n, X, $R_2$, $R_2$, $R_3$, B and B' being defined as above.

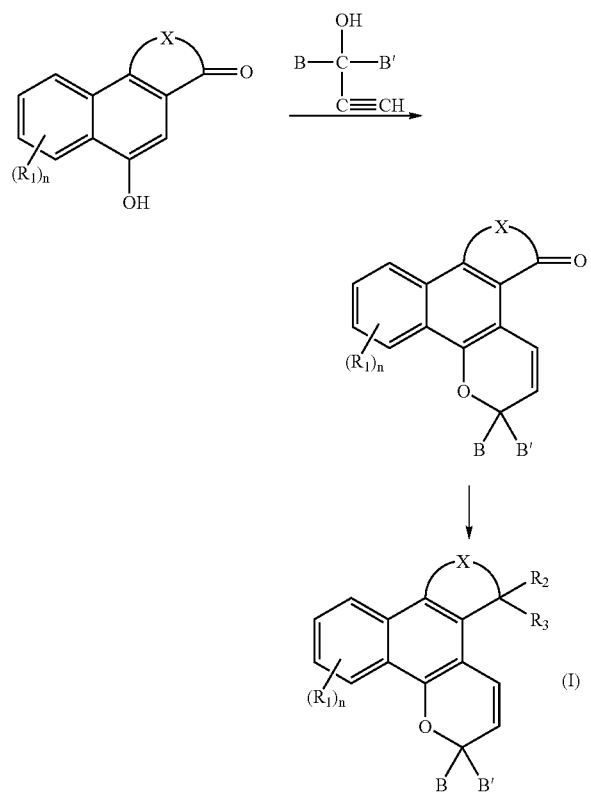

The keto group can be derivatized in the second step of the general reaction outline by generally known methods, such as the reaction with appropriate Grignard reagents.

The inventive compounds can be used in plastic materials or plastic objects of any type and shape for a plurality of purposes, for which the photochromic behavior is of importance. Moreover, a dye of the present invention or a mixture of such dyes can be used. For example, the photochromic naphthopyran dyes of the present invention can be used in lenses, particularly in ophthalmic lenses, lenses for eyeglass of all types, such as ski goggles, sunglasses, motorcycles goggles, visors of helmets and the like. Moreover, the inventive naphthopyrans can also be used, for example, as sun protection in vehicles and residences in the form of windows, protective shutters, coverings, roofs or the like.

To prepare such photochromic objects, the inventive photochromic naphthopyran dyes can be applied by various methods, described in the state of the art, such as those already given in WO 99/15518, on a polymer material, such as an organic synthetic resin material, or embedded therein.

In this connection, a differentiation is made between bulk dyeing methods and surface dyeing methods. A bulk dye method comprises, for example, the dissolving or dispersing of the inventive photochromic compound or compounds in a synthetic resin material, for example, by the addition of the photochromic compound or compounds to a monomeric material, before polymerization takes place. A further possibility of producing a photochromic object is the penetration of the synthetic resin material or materials with the photochromic compound or compounds by immersing the synthetic resin material in a hot solution of the photochromic dye or dyes of the present invention or, for example, by a heat transfer method. The photochromic compound or compounds can also be provided, for example, in the form of a separate layer between adjoining layers of the synthetic resin material, such as a part of a polymeric film. Moreover, the photochromic compound or compounds can also be applied as part of a coating present on the surface of the synthetic resin material. The expression "penetration" is intended to signify the migration of the photochromic compound or compounds into the synthetic resin material, for example, by the solvent-supported transfer of the photochromic compound or compounds into a polymer matrix, by the vapor face transfer or by different types of surface diffusion processes. Advantageously, such photochromic objects, such as eyeglass lenses, can be produced not only by means of the conventional bulk dyeing, but also, in a similar manner, by means of surface dyeing. For the latter variation, a surprising slight tendency to migrate can be achieved. This is of advantage especially for the subsequent finishing steps, since layer detachments and similar defects are drastically reduced, for example, during an anti-reflection coating, due to the lesser back diffusion under vacuum.

Overall, on the basis of the inventive photochromic 2H-naphtho[1,2-b]pyrans, any dyes, which are compatible from a chemical and color point of view, can be applied on or embedded in the synthetic resin material in order to satisfy esthetic points of view as well as medical or fashion points of view. The dye or dyes, specifically selected, can therefore be varied depending on the intended effect as well as on the requirements.

In the following, the synthesis of inventive 2H-naphtho[1,2-b]pyrans, selected by way of example, is explained in detail, these examples serving, of course, only as illustration and do not limit the scope of the present invention.

EXAMPLES

Example 1

Synthesis of spiro-9'-xanthene-5-[2-(4-methoxyphenyl)-2-phenyl-5,6,7,8-tetrahydro-6,6,7,7-tetramethylphenanthro[9,10-b]pyran]

i) Aluminum chloride (24.5 g) and 14.5 g of tetramethylsuccinyl anhydride (A. v. Auwers, N. Ungemach, Chem. Ber. 1935, 68, 349) were treated with stirring and cooling with ice water with 14.7 g of methoxynaphthalene. The mixture, after being thawed and stirred overnight, was poured onto ice water. The resulting precipitate was subsequently filtered off. The acid was purified over its sodium salt and recrystallized from acetic acid. The colorless solid (18 g) was identified by means of NMR spectroscopy to be β-(4-methoxy-1-naphthoyl)-α-α-β-β-tetramethylpropionic acid.

ii) The keto acid so obtained (10 g) was heated for 8 hours at 130° to 135° C. with 10 g of potassium hydroxide and 8 g of 80% hydrazine hydrate in 50 mL of diethylene glycol. After the water and the excess hydrazine hydrate were distilled off, the temperature was maintained at 210° C. for 3 hours and subsequently lowered to 90° C., at which temperature the product was poured onto a mixture of 200 g of ice and 50 mL of concentrated hydrochloric acid. The resulting precipitate was filtered off with suction and washed until neutral. The solid subsequently was stirred with 14 mL of dimethylsulfate in 80 mL of 10% sodium hydroxide solution at 40° to 50° C. The ester, formed as an intermediate, was subsequently saponified under reflux. The solution was cooled and acidified and the resulting precipitate was filtered off with suction and washed until neutral. The product (7.5 g) was identified by means of NMR spectroscopy as γ-(4-methoxy-1-naphthyl)-α,α,β,β-tetramethylbutyric acid.

iii) A suspension of 5 g of the acid, obtained in step ii), was treated in 100 mL of anhydrous ether and 2 drops of pyridine with 4 mL of thionyl chloride and refluxed for 1 hour. After cooling, the solvent was distilled off under vacuum and the residue dissolved in 50 mL and, while being stirred and cooled with ice water, treated with 8 mL of tin tetrachloride. The mixture was stirred for 15 minutes and subsequently poured onto a mixture of 100 mL of ice water and 25 mL of concentrated hydrochloric acid. The organic phase was separated off and washed once each with dilute hydrochloric acid, water and ammonium hydroxide solution. After the solvent was distilled off under vacuum, a light yellow residue (4.1 g) remained behind, which was identified by means of NMR spectroscopy as being 1,2,3,4-tetrahydro-9-methoxy-2,2,3,3-tetramethyl-1-oxo-phenanthrene.

iv) The reaction product (4 g), obtained in step iii) was refluxed in a mixture of 20 mL of 48% hydrogen bromide and 20 mL of glacial acetic acid for 3 hours. After cooling, the formulation was poured into water, made alkaline and washed twice with ether. The solution was acidified and the resulting precipitate filtered off with suction and washed until neutral. The product (3.5 g) was identified by means of NMR spectroscopy as being 1,2,3,4-tetrahydro-9-hydroxy-2,2,3,3-tetramethyl-1-oxo-phenanthrene.

v) The phenanthrene derivative (3 g), obtained in step iv), was suspended with 4.6 g of 1-(4-methoxyphenyl)-1-phenyl-1-propinol (produced from 4-methoxybenzo-phenone and sodium acetylide in DMSO) in 100 mL of toluene. After addition of a spatula tip of 4-toluenesulfonic acid, the mixture was refluxed for 2 hours, a solution being formed. After cooling, half the solvent was distilled off under vacuum and the remaining solution chromatographed on aluminum oxide, having a water content of 3%, with a 1:1 mixture of dichloromethane and methane. For the final purification, the crude product was digested in 50 mL of methanol. The solid was filtered off with suction, washed with methanol and dried. The light yellow powder (4.1 g) was identified by means of NMR spectroscopy as being 2-(4-methoxyphenyl)-2-phenyl-5,6,7,8-tetrahydro-6,6,7,7-tetramethyl-5-oxo-phenanthro-[9,10-b]pyran (4 g).

vi) The reaction product (2 g), obtained in step v), was dissolved with stirring in 50 mL of anhydrous THF and treated with two equivalents of 2-phenoxyphenyl magnesium bromide (synthesized from 2-bromodiphenylether and magnesium shavings in THF solution). The mixture was stirred for 10 hours at room temperature and hydrolyzed with aqueous ammonium chloride solution. After addition of 100 mL of dichloromethane, the organic phase was separated off, washed with water and dried over sodium sulfate. After the solvent was distilled off, the residue was digested with methanol. By means of NMR spectroscopy, the residue was identified as being 5-hydroxy-2-(4-methoxyphenyl)-5-(2-phenoxyphenyl)-2-phenyl-5,6,7,8-tetrahydro-6,6,7,7-tetramethylphenanthro[9,10-b]pyran (1.1 g), which was used further as crude product.

vii) The reaction product (0.8 g), obtained in step vi), was cyclized in 30 mL of hot glacial acetic acid by the method of R. G. Clarkson, M. Gomberg, J. Am. Chem. Soc. 1930, page 2881. After the addition of a drop of hydrochloric acid, the temperature was raised to the boiling point for 5 minutes, after which water was added until the reaction solution became cloudy. After cooling, the precipitate was filtered off with suction, washed until neutral and dried carefully. For the final purification, the solid was dissolved in 30 mL of dichloromethane and chromatographed on aluminum oxide, having a water content of 3%, with a 1:1 mixture of dichloromethane and hexane. After digestion with hexane, a beige colored powder (0.3 g) was obtained, which was identified by NMR spectroscopy as being spiro-9'-xanthene-5-[2-(4-methoxyphenyl)-2-phenyl-5,6,7,8-tetrahydro-6,6,7,7-tetramethylphenanthro[9, 10-b]pyran].

Example 2

Synthesis of spiro-9'-fluorene-5-{2-[4-(N-morpholinyl)phenyl]-2-phenyl-5,6,7,8-tetrahydrophenanthro[9,10-b]pyran}

Starting from methoxynaphthalene and succinic anhydride, 1,2,3,4-tetrahydro-9-methoxy-1-oxophenanthrene was synthesized first by a method similar to steps i) to iii) of Example 1 (see W. E. Bachmann and D. W. Holmes, (J. Chem. Soc. 1940, 62, page 2750). The demethylation (step iv) was carried out by the method of G. A. R. Kon and F. C. J. Ruzicka (J. Chem. Soc. 1936, page 187).

Subsequently, the reaction was carried out as in Example 1, with the exception that, in step v), the reaction was carried out with 1-[4-(N-morpholinyl)phenyl]-1-phenyl-1-propinol (synthesized from 4-(N-morpholinyl)benzophenone) (H. Kotsuki, Synthesis 1990, page 1145) and sodium acetylide in DMSO) instead of with 1-(4-methoxyphenyl)-1-phenyl-1-propinol. 2-[4-(N-Morpholinyl)phenyl]-2-phenyl-5,6,7,8-tetrahydro-5-oxo-phenanthro[9,10-b]pyran was obtained which, as in Example 1, was reacted in the subsequent step vi) with 2-biphenylyl magnesium bromide (synthesized from 2-bromobiphenyl and magnesium shavings in THF solution) to form 5-hydroxy-5-(2-biphenylyl)-2-[4-(N-morpholinyl)phenyl]-2-phenyl-5,6,7,8-tetrahydrophenanthro[9,10-b]pyran]. As in Example 1, the cyclization to spiro-9'-fluorene-5-{2-[4-(N-morpholinyl)phenyl]-2-phenyl-5,6,7,8-tetrahydrophenanthro[9,10-b]pyran} (0.3 g) was carried out in the subsequent step vii), as confirmed by NMR spectroscopy.

Example 3

Synthesis of 5-hydroxy-2,2,5-triphenyl-5,6,7,8-tetrahydro-phenanthro[9,10-b]pyran The method was similar to that of Example 2 with the exception that, in step v), the reaction was carried out with 1,1-diphenyl-1-propinol [synthesized from benzophenone and sodium acetylide in DMSO], instead of with 1-[4-(N-morpholinyl)phenyl]-1-phenyl-1-propinol. 2,2-Diphenyl-5,6,7,8-tetrahydro-5-oxo-phenanthro[9,10-b]pyran was obtained, which was reacted, as in step vi) of Example 1, with two equivalents of a 2 molar solution of phenyl magnesium chloride in THF. The crude product thus obtained was chromatographed with dichloromethane on aluminum oxide, having a water content of 3%. The beige colored product (0.5 g) was identified by means of NMR spectroscopy as being 5-hydroxy-2,2,5-triphenyl-5,6,7,8-tetrahydrophenanthro[9,10-b]pyran.

Example 4

Synthesis of spiro-9'-{(9,10-dihydroanthracene)-5-[2,2-bis(4-methoxy-phenyl)]-cyclopenta[f]naphtho[1,2-b]pyran}

Instead of 1,2,3,4-tetrahydro-9-hydroxy-2,2,3,3-tetramethyl-1-oxo-phenanthrene, 4,5-benzo-8-hydroxy-indan-1-one (see T. Sasaki, K. Kanematsu, K. Hayakawa, A. Kondo, J. Org. Chem. 1973, 38, page 4100) was used in step v) of Example 1. The latter was reacted with 1,1,-bis(4-methoxyphenyl)-1-propinol (synthesized from 4,4'-dimethoxybenzophenone and sodium acetylide in DMSO). 2,2-Bis(4-methoxyphenyl)-5-oxo-cyclopenta[c]naphthopyran was obtained which, as in Example 1, was reacted in the subsequent step vi) with 2-benzylphenyl magnesium bromide (synthesized from 2-bromodiphenylmethane and magnesium in THF solution) to 5-(2-benzylphenyl)-5-hydroxy-2,2-bis(4-methoxyphenyl)-cyclopenta[f]naphthopyran. As in Example 1, the cyclization to spiro-9'-{(9, 10-dihydroanthracene)-5-[2,2-bis(4-methoxyphenyl)]-cyclopenta[c]naphtha[1,2-b]pyran} (0.4 g) was carried out in the subsequent step (vii), as confirmed by means of NMR spectroscopy.

The invention claimed is:

1. A photochromic 2H-naphtho-[1,2-b]pyran compound corresponding to formula (I)

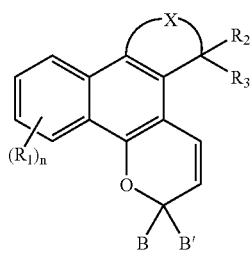

(I)

wherein
X represents a saturated or unsaturated 2 to 4 member chain containing at least one carbon atom and a hetero moiety selected from the group consisting of O, S and $NR_4$, wherein $R_4$ is a linear or branched $C_1$ to $C_6$ alkyl group, a $C_5$ to $C_7$ cycloalkyl group, a phenyl group or a benzyl group, and said at least one carbon atom in X optionally is monosubstituted or disubstituted with at least one substituent selected from the group consisting of $C_1$ to $C_6$ alkyl, $C_1$ to $C_6$ alkoxy, phenyl, bromine, chlorine and fluorine;
$R_1$ is a substituent selected from the group A consisting of $C_1$ to $C_6$ alkyl, $C_1$ to $C_6$ alkoxy, $C_3$ to $C_7$ cycloalkyl optionally containing one hetero atom, phenyl, hydroxy, bromine, chlorine and fluorine;

n is 0, 1 or 2;
$R_2$ and $R_3$ are independently selected from the group G consisting of hydrogen, hydroxy, $C_1$ to $C_6$ alkyl, $C_1$ to $C_6$ alkoxy, $C_3$ to $C_7$ cycloalkyl, unsubstituted, monosubstituted and disubstituted phenyl, unsubstituted, monosubstituted and disubstituted naphthyl, and aromatic groups selected from the group C consisting of benzene, naphthalene, phenanthrene, pyridine, quinoline, furan, thiophene, pyrrol, benzofuran, benzothiophene, indol and carbazol, wherein the substituent or substituents of the phenyl or naphthyl group are selected from the group A; or
$R_2$ and $R_3$ together with the spiro carbon atom form a 5- to 11-membered ring to which one or more aromatic or heteroaromatic ring systems selected from the group C may be annellated; or
$R_2$ and $R_3$ together represent an oxygen atom to form a carbonyl group;
B and B' are independently selected from the groups a), b) and c), wherein
a) consists of mono-, di- and trisubstituted aryl groups selected from the group consisting of phenyl and naphthyl;
b) consists of unsubstituted, monosubstituted and disubstituted heteroaryl groups selected from the group consisting of pyridyl, furanyl, benzofuran-2-yl, benzofuran- 3-yl, thienyl, benzothien- 2-yl or benzothien- 3-yl;
wherein the substituents of the aryl or heteroaryl groups in a) and b) are selected from the group consisting of hydroxy, amino, mono-($C_1$ to $C_6$)-alkylamino, di-($C_1$ to $C_6$)-alkylamino, mono- and diphenylamino in which the phenyl ring is unsubstituted, monosubstituted or disubstituted, piperidinyl, morpholinyl, carbazolyl, unsubstituted, monosubstituted and disubstituted pyrryl, $C_1$ to $C_6$ alkyl, $C_1$ to $C_6$ alkoxy, bromine, chlorine and fluorine, wherein the substitutents on the phenyl or pyrryl groups are selected from the group consisting of $C_1$ to $C_6$ alkyl, $C_1$ to $C_6$ alkoxy, bromine, chlorine and fluorine;
c) consists of groups corresponding to the formulas (V) or (W)

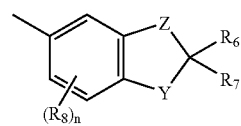

(V)

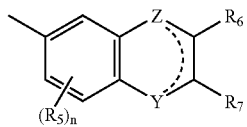

(W)

wherein
Y and Z are independently selected from the group consisting of O, S, CH, $CH_2$ and $NR_8$, wherein $R_8$ is selected from the group D consisting of $C_1$ to $C_6$ alkyl, $C_1$ to $C_6$ acyl and hydrogen;
$R_5$ is selected from the group A; and
$R_6$ and $R_7$ are independently selected from the group consisting of hydrogen and $C_1$ to $C_6$ alkyl,
with the proviso that when Y in formula (V) is $NR_8$, Z is a carbon atom; or
B and B' together form an unsubstituted, monosubstituted or disubstituted fluorene-9-ylidene group wherein the substituents are selected from group A, or
B and B' form a saturated hydrocarbon group which is $C_3$ to $C_{12}$ spiro-monocyclic, $C_7$ to $C_{12}$ spiro-bicyclic or $C_7$-$C_{12}$ spiro-tricyclic.

2. A photochromic 2H-naphtho [1, 2-b]pyran compound according to claim 1, wherein at least one carbon atom in the ring element X is monosubstituted with a substituent or disubstituted with substituents selected from the group consisting of $C_1$ to $C_6$ alkyl, $C_1$ to $C_6$ alkoxy, phenyl, bromine, chlorine and fluorine.

3. A photochromic 2H-naphtho [1, 2-b]pyran compound according to claim 1, wherein the carbon atoms in the ring element X are saturated.

4. A photochromic 2H-naphtho[1,2-b]pyran compound according to claim 3, wherein at least one carbon atom in the ring element X is monosubstituted with a substituent or disubstituted with substituents selected from the group consisting of $C_1$ to $C_6$ alkyl, $C_1$ to $C_6$ alkoxy, phenyl, bromine, chlorine and fluorine.

5. A photochromic 2H-naphtho[1,2-b]pyran compound according to claim 1, corresponding to the formula (II)

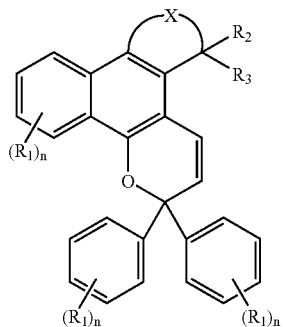

(II)

wherein n, $R_1$, $R_2$, $R_3$ and X are defined as in claim 1, with the proviso that the $R_1$ groups and n may each be the same or different.

6. A photochromic 2H-naphtho[1,2-b]pyran compound according to claim 1, corresponding to the formula (III)

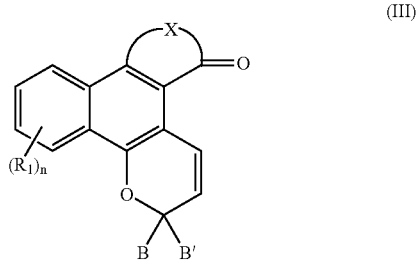

(III)

wherein n, $R_1$, X, B and B' are defined as in claim 1.

7. A photochromic article comprising a synthetic resin body and a photochromic amount of a 2H-naphtho[1,2-b]pyran compound according to claim 1.

8. A photochromic article according to claim 7, wherein said synthetic resin body is an ophthalmic lens.

* * * * *